(12) United States Patent
Haran

(10) Patent No.: US 9,201,018 B2
(45) Date of Patent: Dec. 1, 2015

(54) OPTIMIZED SPATIAL RESOLUTION FOR A SPECTROSCOPIC SENSOR

(71) Applicant: Frank Martin Haran, North Vancouver (CA)

(72) Inventor: Frank Martin Haran, North Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 52 days.

(21) Appl. No.: 14/139,303

(22) Filed: Dec. 23, 2013

(65) Prior Publication Data

US 2015/0177155 A1 Jun. 25, 2015

(51) Int. Cl.
*G01N 21/86* (2006.01)
*G01N 21/3581* (2014.01)
*G01J 3/42* (2006.01)
*G01N 21/27* (2006.01)

(52) U.S. Cl.
CPC . *G01N 21/86* (2013.01); *G01J 3/42* (2013.01); *G01N 21/27* (2013.01); *G01N 21/3581* (2013.01); *G01N 2021/869* (2013.01); *G01N 2021/8663* (2013.01); *G01N 2201/061* (2013.01); *G01N 2201/08* (2013.01)

(58) Field of Classification Search
CPC ........ G01J 3/42; G01N 21/3581; G01N 21/86
See application file for complete search history.

(56) References Cited

U.S. PATENT DOCUMENTS

| | | | |
|---|---|---|---|
| 4,542,297 A * | 9/1985 | Hold | 250/360.1 |
| 4,770,538 A | 9/1988 | Orkosalo | |
| 4,928,013 A | 5/1990 | Howarth et al. | |
| 5,066,865 A * | 11/1991 | Wennerberg | 250/559.01 |
| 5,164,603 A * | 11/1992 | Hartman et al. | 250/559.46 |
| 5,548,120 A * | 8/1996 | Parker et al. | 250/341.7 |
| 5,795,394 A | 8/1998 | Belotserkovsky et al. | |
| 6,059,931 A | 5/2000 | Hu et al. | |
| 6,080,278 A | 6/2000 | Heaven et al. | |
| 6,483,582 B2 | 11/2002 | Modlin et al. | |
| 6,744,516 B2 | 6/2004 | DiDomenico et al. | |
| 6,906,781 B2 | 6/2005 | Berger | |
| 7,196,771 B2 | 3/2007 | Berger | |
| 7,291,856 B2 | 11/2007 | Haran et al. | |
| 7,382,456 B2 | 6/2008 | Tixier et al. | |
| 7,494,567 B2 | 2/2009 | Haran | |
| 7,811,417 B2 | 10/2010 | MacHattie et al. | |
| 7,868,296 B2 | 1/2011 | Haran | |
| 2002/0036775 A1 | 3/2002 | Wolleschensky et al. | |
| 2008/0302707 A1 * | 12/2008 | Bourely | B07C 5/34 209/577 |
| 2011/0222658 A1 | 9/2011 | Radley | |

* cited by examiner

*Primary Examiner* — David Porta
*Assistant Examiner* — Mindy Vu
(74) *Attorney, Agent, or Firm* — Cascio Schmoyer & Zervas

(57) ABSTRACT

Scanning sensor for measuring properties of continuous flat sheet, that is moving in the machine direction, employs an IR radiation source for directing a beam of incident IR radiation that impinges the sheet. The IR source has elongated lamp filament that generates IR radiation and the corresponding spot size formed on the sheet has elongated dimensions with its long axis being aligned with the machine direction. Aligned with the MD maximizes sensor spatial resolution in the cross direction. The sensor can employ a receiver having rectangular geometry with its long axis being aligned also in the MD. Scanning sensor can operate in the reflective, transmissive, or offset transmission mode to monitor characteristics of flat sheets, particularly of paper or plastic products.

16 Claims, 6 Drawing Sheets

OPTIMIZED SPATIAL RESOLUTION FOR A SPECTROSCOPIC SENSOR

FIELD OF THE INVENTION

The present invention generally relates to optical sensors and more particularly to optimized cross direction spatial resolution for spectroscopic sensors used for measuring characteristics of flat sheet products including paper and plastics.

BACKGROUND OF THE INVENTION

During manufacture or flat paper and plastics products, various sheet properties of multi-layered and single layer sheets can be detected with visible and infrared radiation while the sheet-making machine is operating. Characteristics of the sheet including composition, basis weight, coating weight, moisture content, opacity and layer thicknesses can be measured by sensors which detect the amount of radiation that the sheets absorb, transmit or reflect from a beam of infrared light or other radiation. A typical sensor includes an infrared (IR) radiation source that directs a beam of IR radiation towards a sample and the beam is transmitted through beam conditioning optics, such as collimating lenses and/or focusing lenses. These lenses condition the optical radiation for optimal sensor efficiency. The optics in front of the detectors typically comprises focusing lenses and those adjacent to the sample are typically collimating or focusing lenses. IR radiation is partly absorbed, reflected and transmitted by the sample depending on its various properties. A beam splitter splits the IR radiation into two separate beams with each beam being directed to separate band pass filters that are positioned and aligned immediately before detectors. The hand pass filters are configured to pass IR radiation at selected regions of the infrared spectrum. IR radiation, which is not within the selected region of the spectrum, is reflected by the filters back to the beam splitter. Adsorption-type filters can be used although they are less efficiency that the band pass filters which are interference-type filters. Instead of employing a beam splitter which requires a multiplexing arrangement, the sensor can use a rotating filter-wheel assembly. For example, a circular array of filters rotating around a shall or pivot is positioned to the side of the optical path defined by IR radiation reflected from the sample such that a circle drawn through the centers of the filters passes through the center of the optical path. As the filter-wheel rotates, different filters are introduced into and removed from the optical path.

Depending on the intensity of the radiation detected, the detector generates an analog electrical signal that may be converted to a digital signal for observation. The described sensor arrangement can measure different properties of the sample under observation. For instance, in the thickness measurement of thin plastic films, one of the two infrared band pass filters only passes infrared radiation having wavelengths in a selected region of the infrared spectrum. This first region of the spectrum is called the "reference" region, and the associated detector is called the "reference" detector. The reference channel spectral range is located in a specific region of the IR spectrum, which is not associated with a signature absorption band of the material or materials, which the film is composed of. This reference channel however should be indicative of all other optical loss mechanisms in the sensor system and sheet that are not indicative of the optical absorption of the material being sensed. These other properties may include such things as scattering loss from the sheet or the insertion losses of the optical components used.

Similarly, in papermaking, it is well known to continuously measure certain properties of the paper material in order to monitor the quality of the finished product. These on-line measurements often include basis weight, moisture content, gloss, and sheet caliper. The measurements can be used for controlling process variables with the goal of maintaining output quality and minimizing the quantity of product that must be rejected due to disturbances in the manufacturing process.

Generally, on-line measurements of sheet properties are made by scanning sensors that travel back and forth across the width of the sheet in the cross-machine direction (CD). In the manufacturing of a flat sheet of paper, the cross-machine direction uniformity is a critical issue. The scanning sensors are located downstream of actuators that are controlled to adjust the sheet properties. The scanning sensors collect information about the sheet properties to develop a property profile across the sheet and provide control signals to the appropriate actuators to adjust the profile toward a desired target profile in a feedback loop. In practice, the actuators provide generally independent adjustment at adjacent cross-directional locations of the sheet, normally referred to as slices or profile zones.

The sensors include a radiation source that typically comprises a broadband infrared source and a receiver with one or more detectors with the wavelength of interest being selected by narrow-band filters such as, for example, an interference type filter. The sensor gauges used fall into two main types: the transmissive type in which the source and detector are on opposite sides of the web and, in a scanning gauge, are scanned in synchronism across it, and the scatter type (typically called "reflective" type) in which the source and detector are in a single head on one side of the web, the detector responding to the amount of source radiation scattered from the web.

SUMMARY OF THE INVENTION

The present invention is based in part on the recognition that the spatial resolution of infrared spectroscopic sensors is dictated by the radiation source and receiver dimensions and by their fields of view. The present invention optimizes the source's design by aligning the long dimensions of the source lamp filament in the machine direction of a scanning sensor system and at the same time preferably using a rectangular geometry on the receiver with the long axis thereof being aligned also in the MD. In this fashion, the areas of the source and receiver are designed to maximize the cross direction resolution. The incident radiation beam from the infrared radiation source illuminates a small spot size (the area measured on the sheet) on the flat product surface and analysis thereof yields more precise and detail information of the sheet properties of interest.

In one aspect, the invention is directed to a sensor for measuring at least one selected component in a continuous sheet composition having a length and width and that is moving in a machine direction (MD) which is parallel to the sheet length wherein the sheet has a first surface and a second surface that is opposite to the first side that includes:

an infrared (IR) radiation source for directing a beam of incident infrared radiation to the first surface of the sheet wherein the source has a filament that emits IR radiation having an elongated beam profile that impinges on the first surface with an impinging elongated profile; and a detector operable to receive IR radiation that emerges from the second surface of the sheet wherein (i) the impinging elongated profile has a length that is aligned parallel with the MD to maximize detector spatial resolution in the cross direction (CD) or (ii) the detector comprises at least one detector element having a length that is aligned parallel in the MD. In a preferred embodiment, both the impinging elongated profile has a length that is aligned parallel with the MD and the detector comprises at least one detector elements having a length that is aligned parallel in the MD. That is, both the IR radiation source and the IR detector have rectangular fields of view to obtain maximum CD resolution.

In another aspect, the invention is directed to a system for continuous online measurement of a characteristic of a moving sheet that is traveling lengthwise in the machine direction (MD) includes:

an infrared (IR) radiation source which emits radiation from an elongated filament such that an incident elongated beam of IR radiation is directed on a first side of the sheet wherein the IR radiation source travels over the cross direction (CD) of the moving sheet;

a receiver operable to detect radiation emerging from the moving sheet and provides electrical detection signals and wherein the receiver travels over the CD of the moving sheet wherein (i) the long axis of the elongated beam is aligned parallel with the MD or (ii) the receiver comprises at least one detector element having a length that is aligned parallel with the MD; and a processor that receives the electrical detection signals and that is operable to determine at least one property of the sheet In a further aspect, the invention is directed to a method of measuring at least one property of a sheet that is traveling lengthwise in the machine direction (MD) that includes the steps of:

(a) directing a beam of infrared (IR) radiation from an IR radiation source having an elongated filament that emits IR radiation having an elongated beam profile at the moving sheet such that impinging IR radiation has an impinging elongated profile;

(b) measuring radiation emerging from the sample and generating electrical signals therefrom wherein (i) the impinging elongated profile has a length that is aligned parallel with the MD such that the orientation enhances the spatial resolution or (ii) step (b) employs a receiver that has at least one detector element having a length that is aligned parallel with the MD; and (c) determining at least one property of the sample from the electrical signals.

DETAILED DESCRIPTION OF THE PREFERRED EMBODIMENTS

The present invention relates to a sensor device for detecting properties of a composition, especially material that is in the form of a film, web or sheet. While the sensor will be illustrated in measuring properties of paper, it is understood that the sensor can be employed to detect a variety of components in a number of different flat materials including, for example, coated materials, plastics, fabrics, and the like.

Figure 1A:
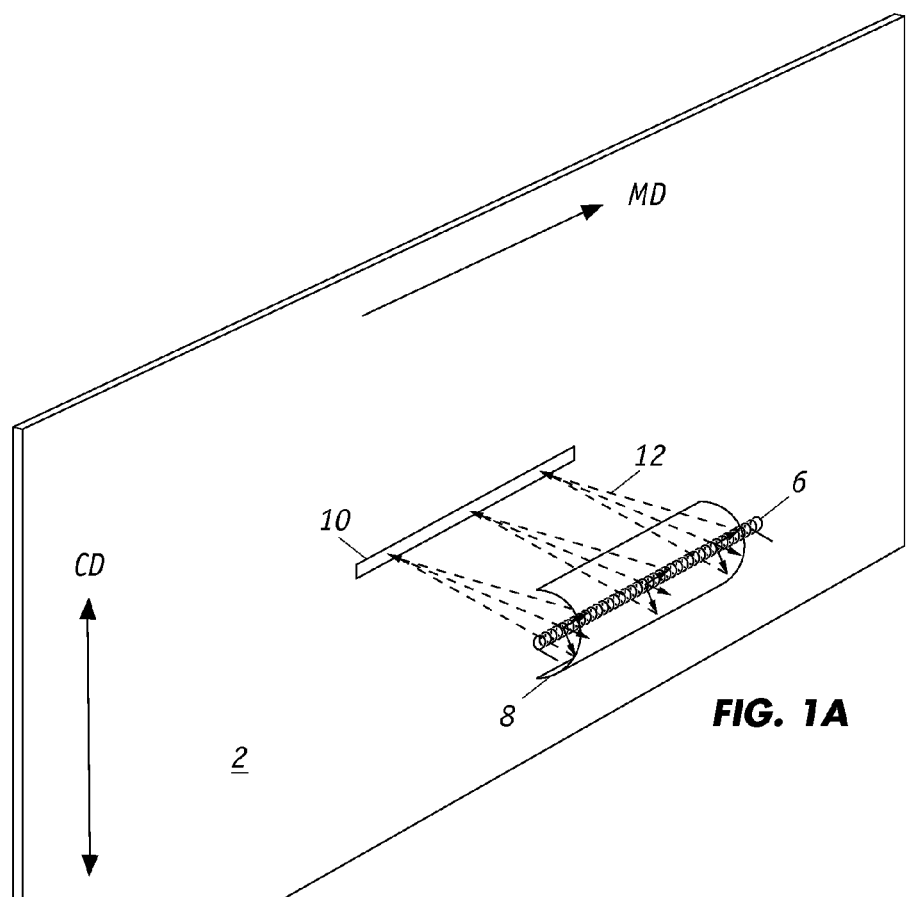
FIGS. 1A and 1B are perspective and side views of an infrared sensor emitting a beam of radiation onto the surface of a moving sheet.
Figure 1B:
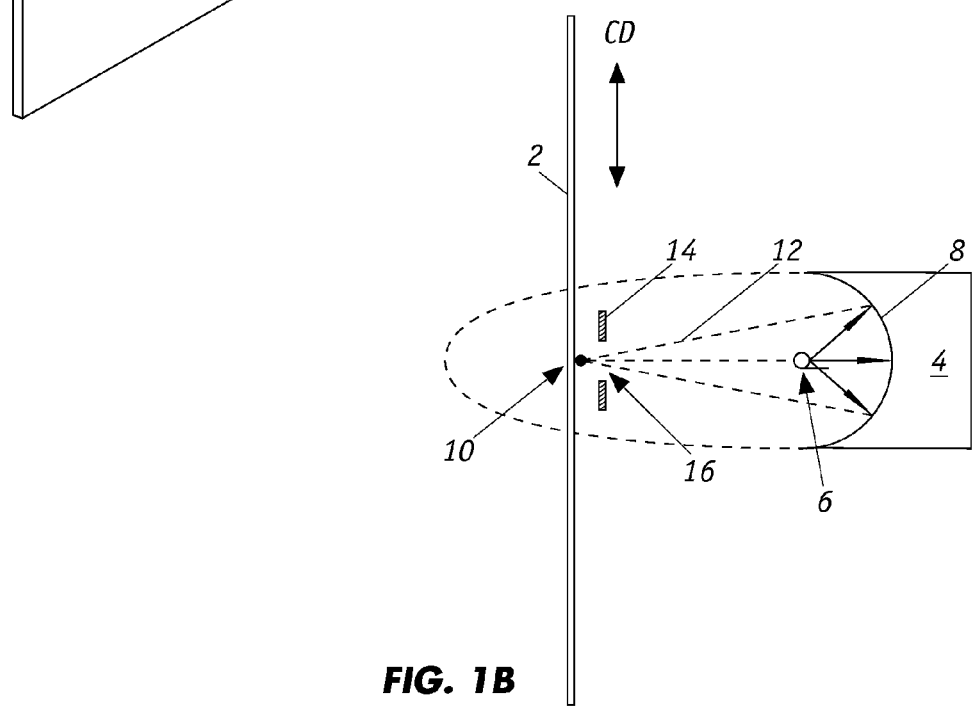

FIGS. 1A and 1B show a continuous sheet or web 2 that is moving lengthwise along the machine direction. An infrared radiation source 4 such as a tungsten halogen lamp (THL) includes an elongated filament 6 that is located at the foci of the elliptical reflector 8. The filament is typically configured as a coil. In this fashion, elliptical reflector 8 re-directs IR rays 12 to converge to form an elongated incident beam 10 with an elongated profile on the top surface of sheet 2. Filament 6 is preferably 5 to 30 mm in length; the elongated beam 10 impinging on sheet 2 preferably has a length of 5 to 30 mm. As shown in FIG. 1B, an IR energy modulator 14 that is positioned before the second foci of elliptical reflector 8 can be employed to provide a high level of IR energy modulation. Modulator 14 preferably comprises a mechanical chopper with one or more elongated or rectangular slots 16 that are aligned parallel to the long axis of elongated beam 10. An advantage of having the long axis of elongated beam 10 aligned parallel with chopper slots 16 is that maximum chopping frequency can be achieved for the mechanical constraints such as motor speed and slot width. Suitable chopper include tuning forks, shutters, and chopper wheels that are equipped with a plurality of radial slots, and which is described in U.S. Pat. No. 4,770,538 to Orkosalo, and that is incorporated herein by reference.

Figure 2:
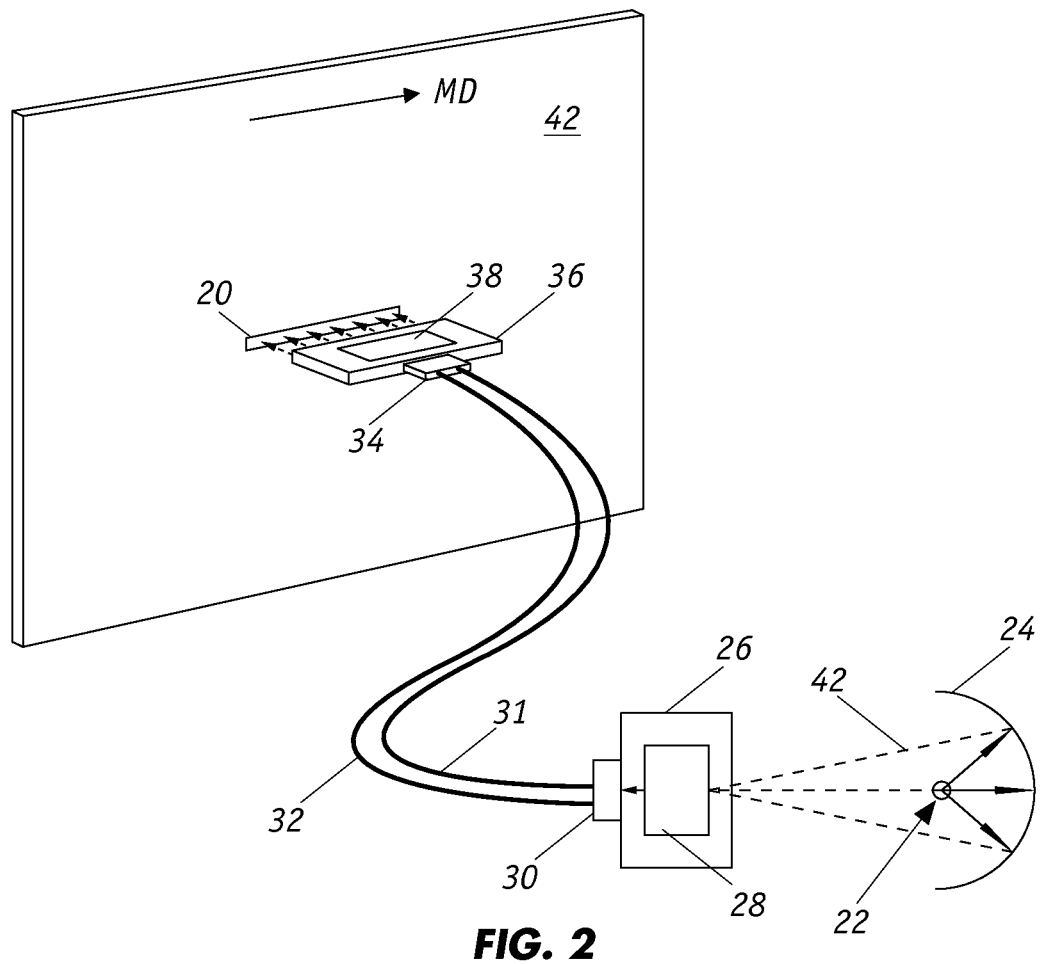
FIG. 2 shows an imaging optics arrangement to image a beam from of an infrared radiation source to a material being measured.

FIG. 2 illustrates an optical technique for imaging an elongated beam 20 to the surface of moving sheet 42 so that beam 20 is aligned with the MD of moving sheet 42. The image transmission optics includes an IR source optical head 26 with coupler 30 and a projection optical head 36 with coupler 34. Couplers 30 and 34 are connected to a linear array of optical fibers 31,32. IR rays 42 that are generated by filament 22 of a THL are focused by elliptical reflector 24 to form an elongated beam that is by imaged by lens 28 into linear array of optical fibers 31,32. Thereafter, the transmitted radiation is imaged by 38 lens as an elongated beam 20 and projected onto sheet 42. The long axis of beam 20 is parallel to the MD of sheet 42. Instead of using a linear array of optical fibers, other radiation transmitting channels such as waveguide or light pipe can be employed.

The arrangement illustrated in FIG. 2 can be incorporated into a sensor system employed to monitor paper quality by scanning the apparatus over a moving sheet of paper during production. Projection optical head 36 would move continuously back-and-forth along the CD relative to moving sheet 42. The light source 22,24 and other devices of the sensor system such as the signal processing components can be located remote from the hostile environment that is usually associated with the sheet making process. The linear array of optical fibers 31,32 can be part of a cable take-up mechanism that manage the fiber while projection optical head 36 is being moved as well as to preserve the overall bend length and radius.

Figure 3:
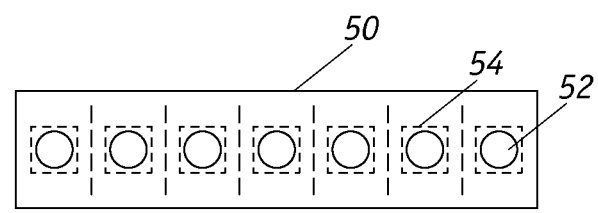
FIG. 3 shows a linear array of detectors.

The sensor device of the present invention includes a receiver that detects radiation that emerges, that is, reflected from or transmitted through the product being measured. FIG. 3 depicts a detector device 50 with a linear array of IR sensors for detecting radiation emerging from a sheet. The array includes a plurality of sensors 52 that are mounted and bonded within a detector module. The rectangular-shaped array is scaled to image the entire illuminating profile of the emerging light. Each sensor 52 can have an associated bandpass filter 54 that can be selected so that it passes IR in a separate region of the IR band. Suitable IR sensors include InGaAs photovoltaic sensors from Hamamatsu Photonics K.K. (Japan) or Teledyne Judson Technologies (Montgomeryville, Pa.). Generally, any suitable photo-detector such as, for example, photoconductive, photovoltaic, pyroelectric type IR sensors can be employed.

Figure 4:
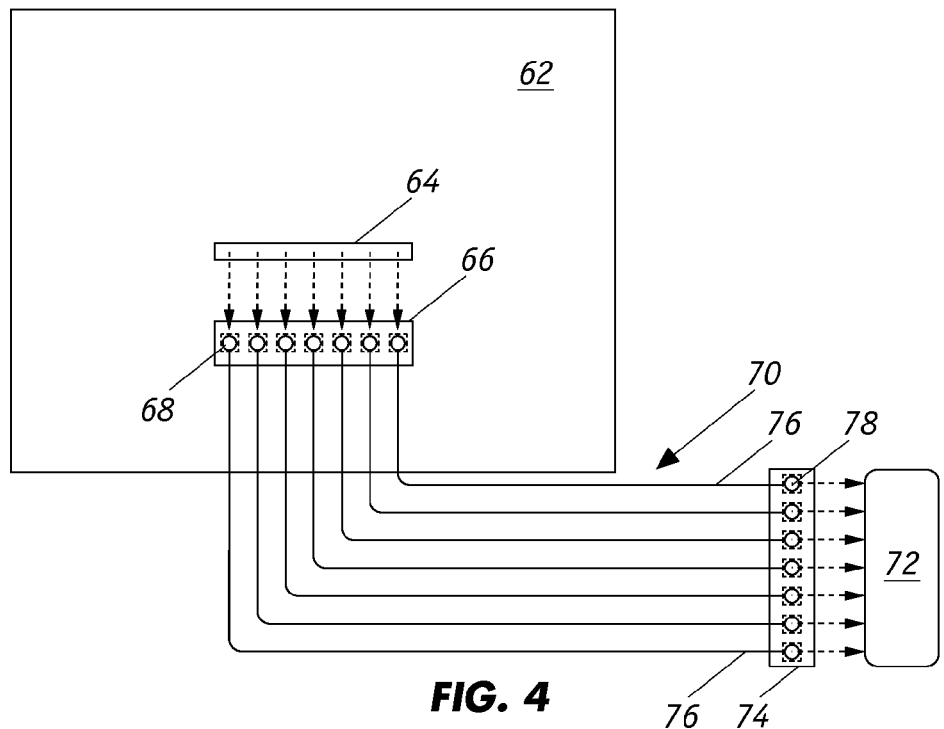
FIG. 4 shows a linear array of optical fibers to transport light that is reflected from or transmittal through material being measured.

FIG. 4 depicts a radiation transmission device with an array 70 of optical fibers or optical fiber bundles 76 that is used to transport emerging light from sheet 62 to individual detectors. The radiation transmission includes rectangle-shaped, light receiving module 66 that is equipped with an array of radiation directing optics 68, such as mirrors and/or lenses, which captures radiation. In operation, an elongated beam 64 that emerges from sheet 62 is captured by light receiving module 66, transported through an array 70 of optical fibers 76 and directed by a plurality of directing optics 78, which are housed in module 74, into a radiation receiver 72 where the intensities of the beam at different wavelengths are measured. The long axis of beam 64 is parallel to the MD of sheet 62. Alternatively, each of the optical fibers 76 in the array 70 can be coupled directly to corresponding detectors without using coupling optics.

Figure 5:
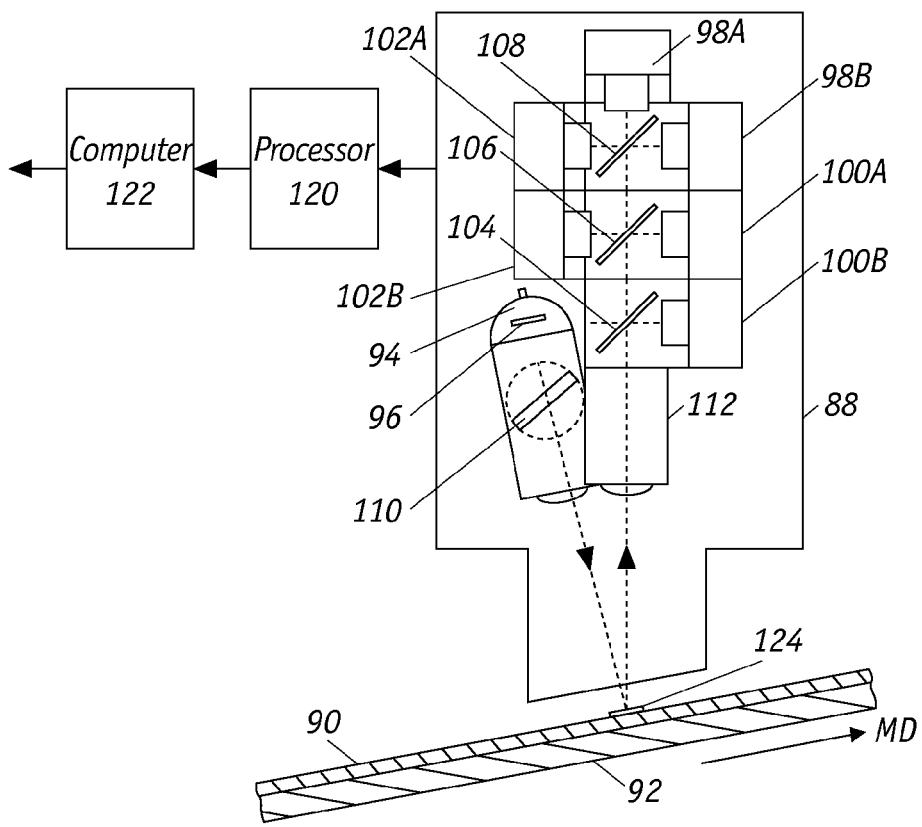
FIGS. 5 and 6 show sensor devices operating in the reflective mode.

FIG. 5 depicts an IR sensor 88 operating in the reflective mode that is used, for instance, to measure the amount of the coating material 90 applied to the base paper sheet 92, which is moving in the MD. The sensor 88 includes a tungsten-halogen source 94 having a filament 96 that provides continuous wave radiation in the visible and infrared regions and a detector assembly of a plurality of IR detectors. The number of IR detectors employed depends on the number of properties being measured. The broadband infrared energy 94 is directed at the sheet 92 at an angle that minimizes sensitivity to sheet flutter and surface characteristics. Typically, when sensor 88 is employed to measure the concentrations of one or more components in a sheet material, a reference and associated measurement detector is configured to measure each component's concentration. Thus, IR sensor 88 with six channels can be employed, for instance, to monitor the concentration of three substances in the composition in coating material 90. The first property is measured by first measure filter/detector 98A and reference filter/detector 98B. The second property is second measured by measure filter/detector 100A and reference filter/detector 100B. The third property measured by third measure filter/detector 102A and reference filter/detector 102B. The energy reflected from the sheet is wavelength-analyzed hr passing the beam through the beam splitters 104, 106, and 108 and the appropriate filters to the individual detectors. This configuration of the optical analyzer comprising the beam splitters, filters, and detectors insures that all detector signals originate from the same location on the sheet, so that at any given time all of the information needed for accurate measurement is available.

Filament 96 is oriented so that its long axis is aligned with the machine direction of base paper sheet 92 so as to form an elongated illumination 124 on the surface of coating material 90 that is also aligned with the MD. In operation, radiation generated by filament 94 is modulated by an infrared enemy modulator 110, which can be a rotating light chopper, for instance. Radiation that is reflected from coating material 90 is directed in the detectors of sensor 88. A radiation transmission device 112 such as that shown in FIG. 4 can be employed to capture the elongated beam reflected from coating material 90.

The output of each of the detectors (both measure and reference) is transmitted to signal processing, circuitry in processor 120. Demodulated and amplitude averaged detector signals are then measured by the signal processing circuitry, digitized and led to the process control computer 122. The computer computes the properties of interested on the base sheet 92 utilizing the standard equations and techniques which are described for example in U.S. Pat. No. 7,494,567 to Haran, U.S. Pat. No. 7,382,456 to Tixier et al., and U.S. Pat. No. 7,868,296 to Haran et al, which are incorporated herein by reference.

Figure 6:
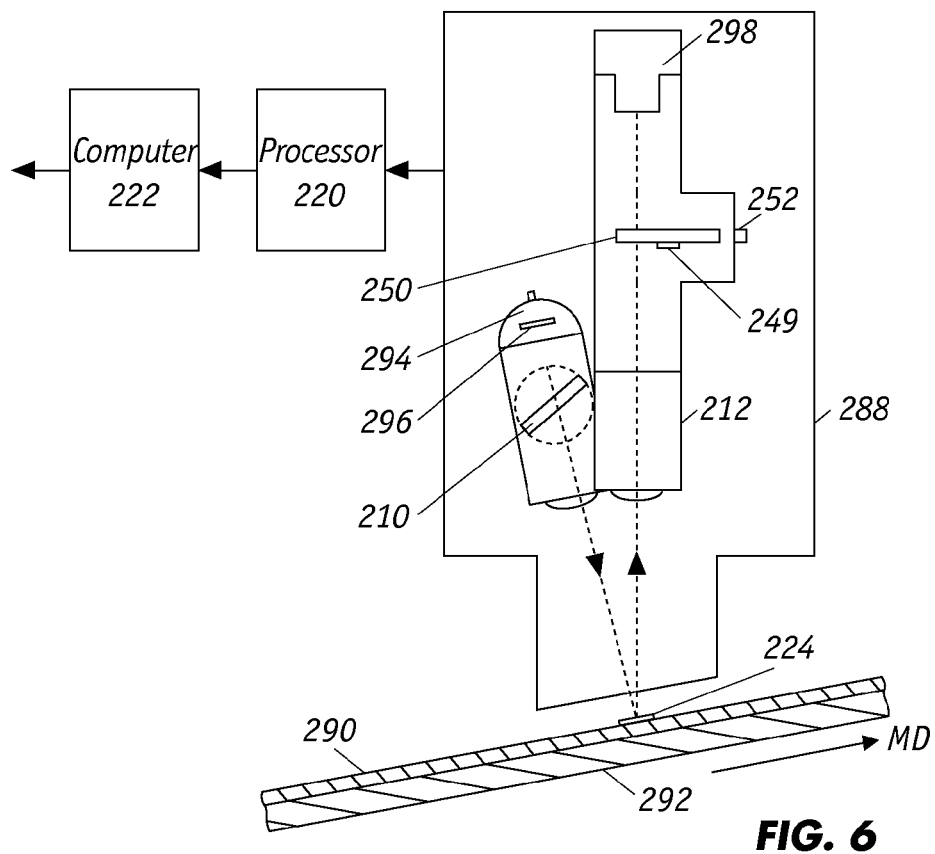
Figure 7:
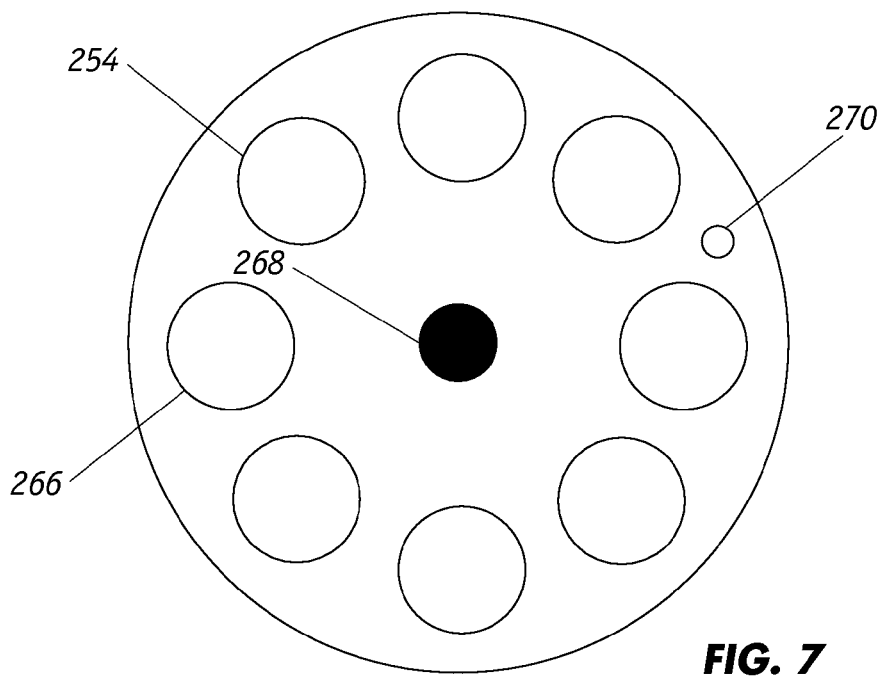
FIG. 7 shows a top view of spectral wheel.

FIG. 6 depicts an IR sensor 288 operating in the reflective mode which employs a spinning filter wheel and that is used, for instance, to measure the amount of the coating material 290 applied that is on base paper sheet 292. Sensor 288 includes a tungsten-halogen source 294 having a filament 296 that provides continuous wave radiation and a single detector 298. A spinning filter wheel 250 that is powered by a motor 249 spins the wheel about an axis and a synchronizing detecting device 252 tracks the position of the of the wheel and rotational speed. FIG. 7 depicts a spinning filter wheel which contains a plurality of light filters 254, 266 about a central axis 268 with each filter designed to allow light of a specific wavelength or wavelength range to pass through it. Eight filters are illustrates, the number of filters being dependent on the number of characteristics being monitored. In this embodiment, four properties can be detected using 4 sets of reference and measurement filters. The wheel includes a synchronizing mark 270 that, when detected by synchronizing detector 252 (FIG. 6).

Broadband infrared radiation 294 is directed at sheet 292 and the reflected energy from the sheet is wavelength-analyzed by passing the beam through a filter of spinning filter wheel 250 and into detector 298. Filament 296 is oriented so that its long axis is aligned with the machine direction of base paper sheet 292 so as to form an elongated illumination 224 on the surface of coating material 290 that is also aligned with the MD. In operation, radiation generated by filament 294 is modulated by an infrared energy modulator 210. Radiation that is reflected from coating material 290 is directed to detector 298. A radiation transmission device 212 such as that shown in FIG. 6 can be employed to capture the elongated beam reflected from coating material 290.

The outputs from detector 298 (at the various measure and reference wavelengths) are transmitted to signal processing circuitry in processor 220. Demodulated and amplitude averaged detector signals are then measured by the signal processing circuitry, digitized and fed to the process control computer 222.

Figure 8:
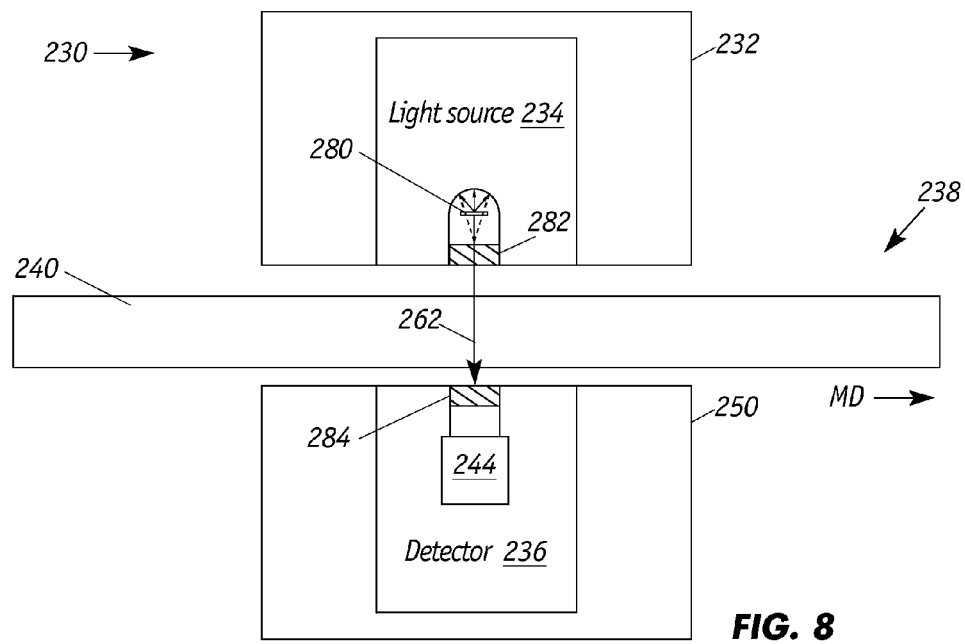
FIG. 8 shows a sensor device operating in the transmissive mode.

FIG. 8 illustrates a sensor that is configured to operate in the transmissive mode where the radiation source and radiation detector are direct opposite sides of web 238. Optical sensor 230 includes an upper scanner head 232 housing light source 234 and a lower scanner head 250 housing detector 236. Sensor 230 measures characteristics of a moving web 238 that comprises a layer of material 240 that is transmissive to radiation. The upper and lower scanner heads 232, 250 are aligned and their movement is coordinated in the cross direction. Filament 280 is oriented so that its long axis is aligned with the machine direction of moving web 238 so as to form an elongated beam that is imaged by lens 282 onto material 240. The foci of the elliptical reflector can also be used to image the beam. Specifically, incident light 262 from light source 234 passes through material 240 and enters receiver 236 through lens 284. It is expected that the elongated shaped of the incident light remains somewhat aligned in the MD as the radiation is passes through material 240 so that exiting radiation that is directed into spectrometer 244, for instance, retains its alignment to the MD. Instead of a spectrometer, a filter-beam splitter stack as shown in FIG. 5 can be employed.

Figure 9:
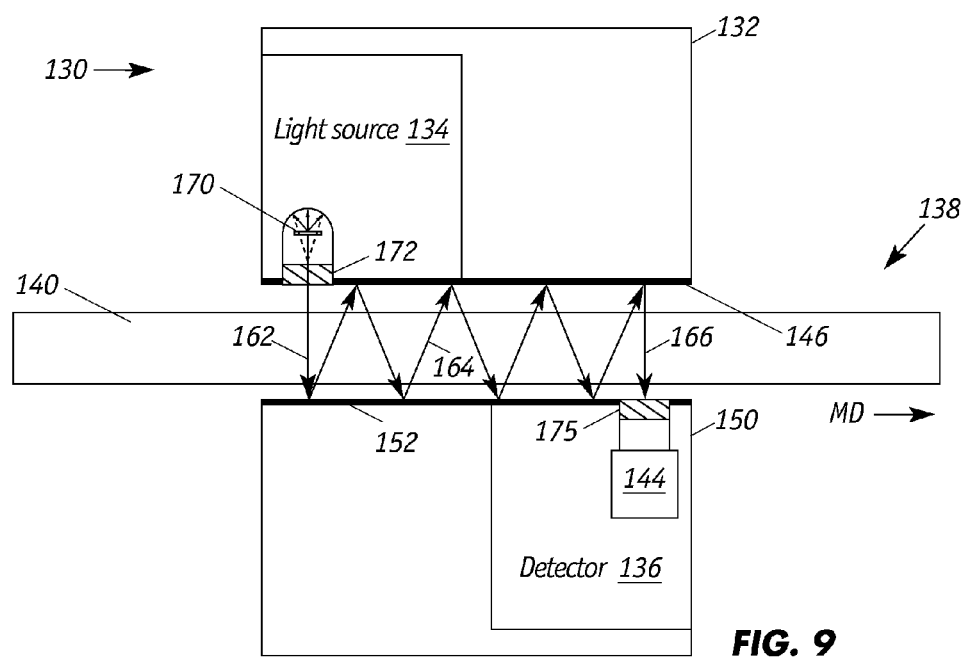
FIG. 9 shows sensor device operating in the offset mode.

FIG. 9 illustrates a sensor that is configured to operate in the offset transmission geometry where the radiation source and radiation detector are laterally offset from one another with respect to the path of a flat product being monitored. Optical sensor 130 includes an upper scanner bead 132 that houses light source 134 and a lower scanner head 150 that houses detector 136. Sensor 130 measures characteristics of a moving web 238 that comprises a layer of material 140 that is transmissive to radiation. A reflector 146 is secured to the lower surface of head 132. The reflector 146 can be either specular or diffusive depending on the application. For measuring paper product, a diffusive reflector is preferred. Similarly, lower scanner head 150 has a reflective surface 152, which can be either specular or diffusive, is positioned adjacent to the lower surface of the layer of material 140. The upper and lower scanner heads 132,150 are aligned so that mirror 146 of the upper scanner bead 132 is parallel with and faces reflective surface 152. In addition, the movement of the upper and lower scanner heads 132,150 is coordinated in the cross direction so that light is reflected between reflective surfaces 146 and 152 as radiation 164 propagates through layer of material 140. Filament 170 is oriented so that its long axis is aligned with the machine direction of moving web 138 so as to form an elongated beam that is imaged by lens 172 onto material 140. Specifically, incident light 162 from light source 134 is reflected by lower reflective surface 152 and upper mirror 146 multiple times (shown as reflected radiation 164) before the light enters receiver 136 through lens 175. It is expected that the elongated shaped of the incident light remains aligned in the MD as the radiation is reflected through material 140 so that exiting radiation 166 that is directed into spectrometer 144, for instance, retains its alignment to the MD.

Figure 10:
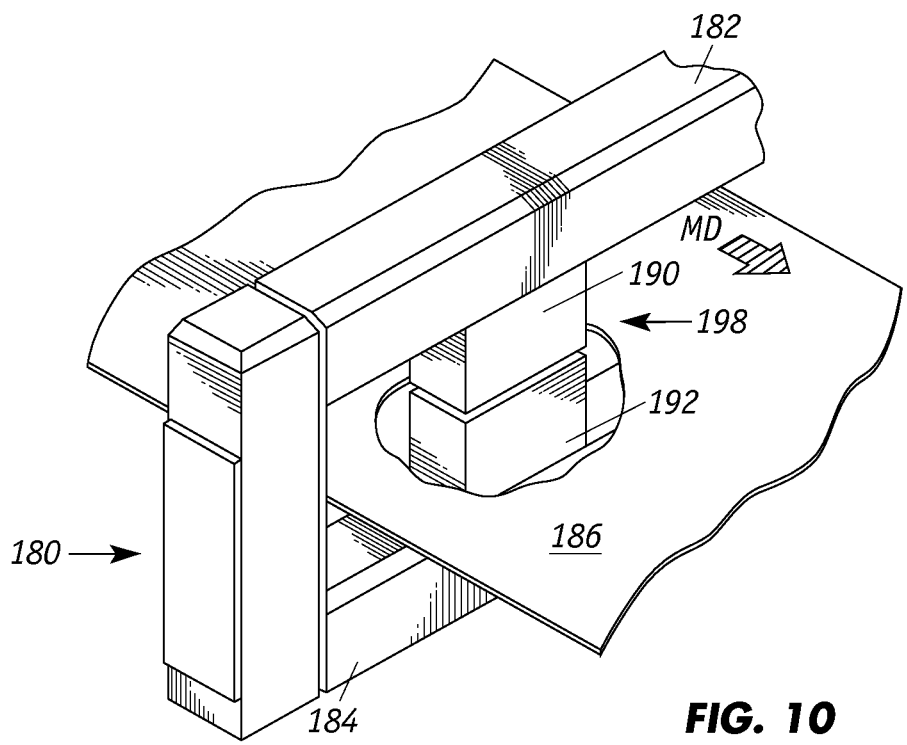
FIG. 10 shows a scanning sensor system for measuring properties a moving sheet.

FIG. 10 illustrates a scanning sensor system whereby the sensor is incorporated into a dual head scanner 198 of scanner system 180 that is employed to monitor one or more properties during continuous paper production. Scanner 198 is supported by two transverse beams 182,184, on which are mounted upper and lower scanning heads 190,192. The operative faces of the lower and upper scanner heads 190,192 define a measurement gap that accommodates sheet 186.

When the sensor is operating in the reflective mode as illustrated in FIG. 5, both the radiation source and receiver are housed within upper scanner head 190. When the sensor is operating in the transmission mode as illustrated in FIG. 8 or 9, the radiation source and receiver are housed within upper scanner head 190 and lower scanner head 192, respectively. It should be noted that in alternative configurations of the offset transmission mode scanning sensor of FIG. 9, the source and receiver are housed in the same head. Finally, when operating in the standard transmissive mode, a radiation source is positioned in the upper scanning head 190 while the radiation receiver is positioned in the lower scanning head 192.

The movement of the dual scanner heads 190, 192, is synchronized with respect to speed and direction so that they are aligned with each other. The radiation source produces an elongated illumination (spot size) on the sheet 186 that is aligned with the MD as the sensor moves repeatedly back and forth in the CD across the width of the moving sheet 186, so that the characteristics of the entire sheet can be monitored.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A sensor for measuring at least one selected component in a continuous sheet composition having a length and width and that is moving in a machine direction (MD) path which is parallel to the sheet length wherein the sheet has a first surface and a second surface that is opposite to the first side that comprises:

an infrared (IR) radiation source for directing a beam of incident infrared radiation to the first surface of the sheet wherein the source has a filament that emits IR radiation having an elongated beam profile that impinges on the first surface with an impinging elongated profile; and a detector operable to receive IR radiation that emerges from the second surface of the sheet wherein (i) the impinging elongated profile has a length that is aligned parallel with the MD to maximize detector spatial resolution in the cross direction (CD) and (ii) the detector comprises at least one detector element having a length that is aligned parallel in the MD.

2. The sensor of claim 1 wherein the detector comprises an array of detector elements such that the array has a long axis that is aligned parallel with the MD.

3. The sensor of claim 1 wherein the IR radiation source is coupled to a radiation transmitting channel so that IR radiation from the source is transmitted through the radiation transmitting channel toward the first surface.

4. The sensor of claim 1 wherein the IR radiation source comprises a filament and directing optics to concentrate and direct the IR radiation at the first surface of the continuous sheet composition.

5. The sensor of claim 3 wherein the radiation transmitting channel comprises an optical fiber.

6. The sensor of claim 1 further comprising a first scanner head housing the IR radiation source and having a first reflector and a second scanner head having a second reflector wherein the first reflector and second reflector define a gap through which the sheet travels wherein the IR radiation source is laterally offset from the detector with respect to the path of the continuous sheet composition and wherein the detector is positioned to detect IR radiation that is reflected by the first reflector and second reflector as the IR radiation propagates through the sheet a plurality of times before being detected by the detector.

7. The sensor of claim 1 wherein the IR source and detector are scanned along the cross direction of the sheet.

8. The sensor of claim 1 comprising means for modulating the beam of incident radiation that includes a rotating light chopper having one or more elongated slots whose long axes are parallel to the beam.

9. The sensor of claim 1 comprising a scanning sensor head that houses optics that directs the beam of incident IR radiation toward the first surface of the sheet, wherein the IR radiation source comprises an incandescent lamp equipped with an elongated filament and wherein the incandescent lamp is located remotely from the scanning sensor head and wherein an optical fiber, through which the IR radiation is transmitted, couples the scanning sensor to the IR radiation source.

10. The sensor of claim 1 wherein the continuous sheet composition comprises paper or plastic.

11. A method of measuring at least one property of a sheet that is traveling lengthwise in a machine direction (MD) path that comprises the steps of:
(a) directing a beam of infrared (IR) radiation from an IR radiation source having an elongated filament that emits IR radiation having an elongated beam profile at the moving sheet such that impinging IR radiation has an impinging elongated profile;
(b) measuring radiation emerging from the sample and generating electrical signals therefrom wherein (i) the impinging elongated profile has a length that is aligned parallel with the MD such that the orientation enhances the spatial resolution and (ii) step (b) employs a receiver that has at least one detector element having a length that is aligned parallel with the MD; and
(c) determining at least one property of the sample from the electrical signals.

12. The method of claim 11 wherein in step (a) the impinging elongated profile defines an elongated spot size that remains parallel to the MD as the IR radiation source is scanned over of the sheet in the cross direction.

13. The method of claim 11 comprising employing a first scanner head housing the IR radiation source and having a first reflector and a second scanner head having a second reflector wherein the first reflector and second reflector define a gap through which the moving sheet travels wherein the IR radiation source is laterally offset from the detector with respect to the path of the moving sheet and wherein the detector is positioned to detect IR radiation that is reflected by the first reflector and second reflector as the IR radiation propagates through the moving sheet a plurality of times before being detected by the detector.

14. The method of claim 11 comprising modulating the beam of IR radiation with a modulator that comprises a rotating light chopper that has one or more elongated slots whose long axes are parallel to the beam.

15. The method of claim 11 wherein the sheet comprises paper or plastic.

16. The method of claim 11 wherein step (a) employs a scanning sensor head that houses optics that directs the beam of IR radiation toward the moving sheet, wherein the IR radiation source comprises an incandescent lamp equipped with an elongated filament and wherein the incandescent lamp is located remotely from the scanning sensor head and wherein an optical fiber, through which the IR radiation is transmitted, couples the scanning sensor to the IR radiation source.

* * * * *